(12) United States Patent
Hamilton et al.

(10) Patent No.: US 12,266,443 B2
(45) Date of Patent: Apr. 1, 2025

(54) METHOD FOR REGISTERING A VIRTUAL REPRESENTATION OF A PATIENT ANATOMY WITH A COORDINATE SYSTEM OF A PHYSICAL PATIENT ANATOMY

(71) Applicant: Brainlab AG, Munich (DE)

(72) Inventors: Christoffer Hamilton, Munich (DE); Nils Frielinghaus, Munich (DE)

(73) Assignee: BRAINLAB AG, Munich (DE)

( * ) Notice: Subject to any disclaimer, the term of this patent is extended or adjusted under 35 U.S.C. 154(b) by 280 days.

(21) Appl. No.: 17/910,308

(22) PCT Filed: Mar. 11, 2021

(86) PCT No.: PCT/EP2021/056240
§ 371 (c)(1),
(2) Date: Sep. 8, 2022

(87) PCT Pub. No.: WO2021/180873
PCT Pub. Date: Sep. 16, 2021

(65) Prior Publication Data
US 2023/0005596 A1    Jan. 5, 2023

(30) Foreign Application Priority Data

Mar. 12, 2020 (WO) ................. PCT/EP2020/056738

(51) Int. Cl.
*G16H 30/20* (2018.01)
(52) U.S. Cl.
CPC .................................. *G16H 30/20* (2018.01)
(58) Field of Classification Search
CPC ...................................................... G16H 30/20
(Continued)

(56) References Cited

U.S. PATENT DOCUMENTS

2010/0152570 A1* 6/2010 Navab .................... A61B 90/36
600/443
2011/0216089 A1* 9/2011 Leung ....................... G06T 7/35
382/284

(Continued)

FOREIGN PATENT DOCUMENTS

| EP | 3533409 | 9/2019 |
|---|---|---|
| WO | 2018129094 | 7/2018 |

(Continued)

OTHER PUBLICATIONS

Van Doormaal, Tristan P.C. et al., "Clinical Accuracy of Holographic Navigation Using Point-Based Registration on Augmented-Reality Glasses", Operative Neurosurgery, Dec. 2019, vol. 17, No. 6, pp. 588-593 (Year: 2019).*

(Continued)

*Primary Examiner* — Michael Tomaszewski
(74) *Attorney, Agent, or Firm* — Gray Ice Higdon

(57) ABSTRACT

The present invention relates to a method for registering a virtual representation of a patient anatomy with a coordinate system of a physical patient anatomy, comprising displaying first overlap data in a head-mounted device, wherein the first overlap data describe from a first perspective onto the physical patient anatomy a first visual overlap between the virtual representation of the patient anatomy and the physical patient anatomy, identifying at least a first area in the first visual overlap and/or at least a first anatomical feature of the patient anatomy in the first visual overlap having at least a minimum degree of alignment between the virtual representation and the physical patient anatomy, displaying second overlap data in the head-mounted device, wherein the second overlap data describe from a second perspective onto the physical patient anatomy a second visual overlap between the virtual representation of the patient anatomy and the physical patient anatomy, and taking into account, (Continued)

during the displaying of the second overlap data, the alignment of the identified first area and/or anatomical feature of the patient anatomy that was identified in the first visual overlap as having at least a minimum degree of alignment between the virtual representation and the physical patient anatomy.

31 Claims, 4 Drawing Sheets

(58) Field of Classification Search
 USPC .......................................................... 705/2–3
 See application file for complete search history.

(56) References Cited

U.S. PATENT DOCUMENTS

| | | | |
|---|---|---|---|
| 2016/0240006 A1* | 8/2016 | Ur ........................... | G06T 19/20 |
| 2018/0185100 A1* | 7/2018 | Weinstein ............... | A61F 2/461 |
| 2019/0254753 A1* | 8/2019 | Johnson .................. | A61B 34/76 |
| 2019/0339525 A1* | 11/2019 | Yanof ..................... | A61B 8/466 |
| 2020/0375666 A1* | 12/2020 | Murphy .................. | A61B 34/20 |
| 2021/0052348 A1* | 2/2021 | Schwägli ............... | A61B 90/39 |

FOREIGN PATENT DOCUMENTS

| | | | | |
|---|---|---|---|---|
| WO | WO-2018129094 A1 * | 7/2018 | ........... | A61B 1/0005 |
| WO | 2018203304 | 11/2018 | | |
| WO | WO-2018203304 A1 * | 11/2018 | ............. | A61B 34/10 |
| WO | 2021180873 | 9/2021 | | |
| WO | WO-2021180873 A1 * | 9/2021 | ........... | G06T 19/006 |

OTHER PUBLICATIONS

Tristan P C Van Doormaal et al, "Clinical Accuracy of Holographic Navigation Using Point-Based Registration on Augmented-Reality Glasses", Operative Neurosurgery, vol. 17, No. 6, May 13, 2019 (May 13, 2019), p. 588-593.

Lin Qinyong et al, "Real-time automatic registration in optical surgical navigation", Infrared Physics and Technology, Elsevier Science, GB, vol. 76, Mar. 25, 2016 (Mar. 25, 2016), p. 375-385.

Un Yat Chung James, "Implementation of the Functional Shape Cortical Brain Surface Analysis Pipeline on a High Performance Computing Environment", Aug. 8, 2016 (Aug. 8, 2016), Retrieved from the Internet: URL:http://summit.sfu.ca/system/files/iritems1/16725/etd9681_YUn.pdf.

European Patent Office, International Search Report and Written Opinion issued in Application No. PCT/EP2021/056240, 20 pages, dated May 25, 2021.

\* cited by examiner

METHOD FOR REGISTERING A VIRTUAL REPRESENTATION OF A PATIENT ANATOMY WITH A COORDINATE SYSTEM OF A PHYSICAL PATIENT ANATOMY

FIELD OF THE INVENTION

The present invention relates to a method for registering a virtual representation of a patient anatomy with a coordinate system of a physical patient anatomy, in particular to a computer-implemented medical method for such a registration, a corresponding computer program, a non-transitory program storage medium storing such a program, and a computer for executing the program, as well as a medical system for registering a virtual representation of a patient anatomy with a coordinate system of a physical patient anatomy.

TECHNICAL BACKGROUND

Augmented reality (AR) is an interactive experience of a real-world environment where the objects that reside in the real world are enhanced by computer-generated perceptual information, in particular visual information. In the medical context, this well-known technology can be applied, e.g. to support medical practitioners by calculating and displaying virtual overlays of medical data in a head-mounted device that can be automatically adapted when the practitioner is moving. With such a head-mounted device comprising a display, existing software of Brainlab AG frees patient data from the 2D screen and brings it into the room. In head-mounted mixed reality, i.e. augmented reality, products are currently developed which overlay virtual representations of anatomy or planning data above a real, physical patient anatomy.

For registering the virtual representation of the patient anatomy with the coordinate system of the physical patient anatomy, the virtual model is currently superimposed on the patient from one viewing direction. Thereafter, the user of the head-mounted device (HMD) moves to another position in the room and realigns the virtual model, i.e. the virtual representation, from the second viewing direction. This procedure is currently repeated from different viewing directions until the user is satisfied and gives a feedback to the system that the registration is completed. As is apparent for the person skilled in the art this registration process changes the coordinates of the virtual representation of the patient anatomy within the coordinate system of the physical patient anatomy due to the movement the displayed virtual representation is caused to do by the user relative to the physical patient anatomy. After the registration is completed, the coordinates of the virtual representation in the coordinate system of the patient anatomy are fixed.

However, the inventors of the present invention have identified that it takes multiple realignments from different directions, which first is cumbersome, and second it is in the current registration systems and methods not possible to see the impact of the realignment from one direction on the alignment from another, e.g. the previous, direction.

As an example, US patent application US 2011/0216089 A1 describes that in augmented reality systems, a user's view of the real world is enhanced or augmented with additional information generated by a computing device. This document also describes the need that the alignment of objects needs to be done in augmented reality. However, the downsides of the current registration practice, as was explained hereinbefore, is not acknowledged by the prior art.

It is, therefore, desirable to provide for an improved method of registration of a virtual representation of a patient anatomy with a coordinate system of a physical patient anatomy.

Aspects of the present invention, embodiments, examples and exemplary steps are disclosed in the following. Different embodiments, examples and exemplary features of the invention can be combined in accordance with the invention wherever technically expedient and feasible.

Moreover, it is emphasized that any feature, element and/or step described in the following with respect to one aspect of the invention equally applies to any other aspect of the invention disclosed herein.

EXEMPLARY SHORT DESCRIPTION OF THE INVENTION

In the following, a short description of the specific features of the present invention is given which shall not be understood to limit the invention only to the features or a combination of the features described in this section.

The disclosed method comprises that a first visual overlap between a virtual representation of a patient anatomy and the physical patient anatomy is displayed to the user by means of a head-mounted device. A head-mounted device may thus have a display on which the virtual representation of the patient anatomy can be displayed while at the same time, the user of the head-mounted device sees the real, physical patient anatomy through the head-mounted device. The display that is used by the head-mounted device may thus be seen as a translucent device through which the user can see the real world surrounding him and at the same time, he can see the objects that are projected or displayed on the display of the head-mounted device. Thus, the presented method is used in the context of mixed reality or augmented reality.

The method further comprises the identification of at least an area or a feature in the patient anatomy in said first visual overlap, which feature and/or area has at least a minimum degree of alignment between the virtual representation and the physical patient anatomy. This identification of a well-aligned area and/or a well-aligned anatomical feature can be done manually by the user, e.g. by manually marking or highlighting the well-aligned area/feature in the displayed visual overlap. Appropriate control means, like e.g. a joystick, for navigating through the mixed reality can be used for this, as the skilled reader will appreciate from this disclosure. Alternatively, this can be done automatically by a processor, calculation unit or algorithm of a medical device of the present invention. In the latter computer-implemented alternative of identifying the well-aligned areas/features, the method can be seen as a computer-implemented medical method for registering the virtual representation with the coordinate system of the real, physical patient anatomy that is positioned on e.g. a patient bed in a preparation room, where the registration is carried out. These aspects of the present invention will be explained in more detail hereinafter in the context of particular embodiments.

The presented method further encompasses displaying second overlap data in the head-mounted device, which relates to a second visual overlap between the virtual representation and the physical patient anatomy from a second perspective. Thus, the method presented herein considers the view of the user of the head-mounted device onto the physical patient anatomy laying in front of him or her from a first perspective and at least for a second perspective, into which the user moves or has moved from the first perspective. Of course, the presented method can also be repeated for a third perspective, a fourth perspective etc. However, as will become apparent from the following disclosure, the presented method advantageously reduces the number of perspectives needed for the registration, due to the consideration of the alignment of the identified first area/first feature that was found to be correct from the first perspective, when displaying the second visual overlay from the second perspective.

The presented method further takes into account, during the displaying of the second overlay data, the alignment of the identified first area and/or anatomical feature of the patient anatomy that was identified in the first visual overlap and from the first perspective as having at least a minimum degree of alignment, i.e. a correct alignment for the user and/or the system automatically identifying said features, between the virtual representation and the physical patient anatomy. Therefore, the well alignment of the identified first area and/or first anatomical feature is not disregarded when realigning the virtual representation and the physical patient anatomy by the user from the second perspective, as is currently the case in the prior art. Instead the method presented herein considers during the displaying the visual overlap from the second perspective the alignment of the first area and/or first anatomical feature. Many different ways of considering this alignment of the identified first area and/or anatomical feature during the display of the second overlap data can be used as different embodiments of the method presented herein.

A first example is that in viewing direction A, i.e. in the first perspective, it is possible to manually or automatically define areas of features as having a correct alignment. These alignments are then considered to be static when realigning the virtual representation with the physical patient anatomy by the user from the second viewing direction B, i.e. from the second perspective. Thus, constraints can be used for the movability of the virtual representation/model, which ensures that the found good alignment of the area/feature identified from the viewing direction A, is kept or at least a reduction thereof is minimized, when the user realigns the model with the anatomy from another perspective.

In a particular example, e.g. a virtual nose is matched exactly with the patient's nose in viewing direction A. The nose is thus identified as having a correct alignment, either by the user or by a computer-implemented embodiment of the method presented herein. When realigning the virtual representation with the physical patient anatomy from viewing direction B, an alignment axis that was previously defined as being correct shall remain fixed, which in the present case is the axis from the head-mounted device in viewing direction A through the nose. Thus, this measure takes into account the alignment of the identified first area/first, i.e. the alignment of the nose, when displaying the visual overlap/overlay from the second perspective to the user. This beneficially ensures that the well alignment found from the first perspective, is not forgotten, neglected or disregarded when the user continues the registration method in the subsequent perspective. This effectively leads to a faster convergence of the registration method. In other words, the registration can be completed much faster as compared to the prior art registration methods.

In a further example, the step of taking into account, during the displaying of the second overlap data, the alignment of the identified first area/anatomical feature, is as follows. The features with the minimum degree of alignment, i.e. with a correct alignment in view direction A, are made visible as virtual information when performing the realignment in viewing direction B. Thus, the real and virtual areas/features identified from direction A are both displayed virtually in the head-mounted device when viewing from direction B. This corresponds to a visual feedback for the user in the second perspective regarding what he/she had used for the registration in the first perspective. In other words, it is suggest to extract the anatomical features, e.g. contours thereof, showing at least a minimum degree of alignment from the real image of the viewing direction A and to overlay them, e.g. transparently, together with their virtual counterparts in the viewing direction B in case that these would e.g. be obstructed by another body part in the real view. In case that the deviation of the alignment for those features would not be visible due to the projection into the viewing direction B, e.g. that the misalignment is in the direction B, one would need to make this deviation clear by other means, e.g. by changing the color of these contours based on the degree of misalignment or artificially altering the direction of the misalignment into one of the dimensions that can easily be observed in the viewing direction B or by overemphasizing the effect by e.g. modifying the size of the virtual or real contour much more than the projection would actually cause.

In another example, the alignment from viewing direction A is shown as a picture-in-picture video when realigning from viewing direction B. The video content is created with a previously, from direction A, recorded screenshot/video combined with the virtual overlays. Again, this measure takes into account the alignment of the identified first area/first, when displaying the visual overlap/overlay from the second perspective to the user. In this way the alignment found from the first perspective, is not neglected when the user continues the registration method in the next perspective. In this way the time needed for registration can be reduced as compared to the prior art.

In addition, analytical or numerical optimizations can be used in particular examples to calculate movements of the virtual representation that keep the identified first area/feature in the same alignment, or minimize a change of that alignment while at the same time bringing a second area/feature in alignment in the second perspective.

Even further examples of how the correct alignment of the identified first area and/or anatomical feature of the patient anatomy is taken into account when displaying the second overlap data in the head-mounted device to the user will be explained in the context of and elucidated with a plurality of embodiments hereinafter.

It should be noted that the "user" as described herein shall be understood as the user of the head-mounted device in which the first overlap data, the second overlap data and possibly also further overlap data are displayed. Note that the presented method can also involve a plurality of users, each wearing such a head-mounted device. This allows a collective registration by the plurality of users. For example, a first user may identify the first area/feature from the first perspective and a second user may identify the second area/feature from the second perspective. Thus, several user inputs from different users may be used for carrying out the method for registering the virtual representation of the patient anatomy with the coordinate system of a physical patient anatomy.

Moreover, the term "minimum degree of alignment" shall be understood as features that have a correct alignment, according to the user and/or the system automatically identifying said features, between the virtual representation and the physical patient anatomy. In other words, such features are considered to be well-aligned with respect to the visual overlay of the virtual representation and the real physical anatomy that is in front of the user of the head-up display. The skilled reader will appreciate that with a correct or good alignment, a high degree of correlation or congruency between the virtual representation and the real anatomy is achieved.

It should be noted that in the context of the present invention the term "virtual representation of the patient anatomy" shall also comprise planning data related to a particular patient anatomy.

It should also be noted that in the context of the present disclosure the term "visual overlap" is used synonymously with the term "visual overlay".

GENERAL DESCRIPTION OF THE INVENTION

In the following section, a description of the general features of the present invention is given, for example by referring to possible embodiments of the invention.

As stated above, it may be desirable to provide for an improved registration of a virtual representation of a patient anatomy with a coordinate system of a physical patient anatomy. This is achieved by the subject matter of the independent claims, wherein further embodiments are incorporated in the dependent claims and the following description.

According to a first aspect, a method for registering a virtual representation of a patient anatomy with a coordinate system of a physical patient anatomy is presented. The method comprises:

a) displaying first overlap data in a head-mounted device, wherein the first overlap data describe from a first perspective onto the physical patient anatomy a first visual overlap between the virtual representation of the patient anatomy and the physical patient anatomy (step S1), b) identifying at least a first area in the first visual overlap and/or at least a first anatomical feature of the patient anatomy in the first visual overlap having at least a minimum degree of alignment between the virtual representation and the physical patient anatomy (step S2), c) displaying second overlap data in the head-mounted device, wherein the second overlap data describe from a second perspective onto the physical patient anatomy a second visual overlap between the virtual representation of the patient anatomy and the physical patient anatomy (step S3), and d) taking into account, during the displaying of the second overlap data, the alignment of the identified first area and/or anatomical feature of the patient anatomy that was identified in the first visual overlap as having at least a minimum degree of alignment between the virtual representation and the physical patient anatomy (step S4).

The method as presented herein sets out in the context of head-mounted mixed reality systems, where virtual representations of an anatomy or planning data are overlaid above a real, physical patient anatomy. The process of registering such a virtual representation of a patient anatomy with a coordinate system of a physical patient anatomy involves that the user aligns the virtual representation and the anatomy from at least two different perspectives by manually moving the virtual representation into the, at least from this perspective, correct and well-aligned position. The user may thus initiate several times a movement of the virtual representation relative to the physical patient anatomy, for example by using a joystick or another user control means.

Such a control means with which the user triggers and/or specifies the desired movement of the virtual representation relative to the physical patient anatomy can be seen in for example the embodiment described in the context of FIG. 2. When the user is satisfied with the alignments of the virtual representation and the physical patient anatomy from two or more perspectives, he completes the registration process.

In the method presented herein, the virtual model is thus superimposed on the patient from one viewing direction by displaying the first overlap data. Moreover, features or areas in the first visual overlap are identified, which fulfil at least a minimum degree of alignment between the virtual representation and the physical patient anatomy. These features are considered to have a correct alignment in the context of the present invention. When the method is described on the computer-implemented side only, than this step may also be implemented as receiving, by the computer, the calculation unit or the processor, identification information describing the at least first area and/or the at least anatomical feature of the patient anatomy in the first visual overlap. When the user has identified the well aligned areas/features, corresponding identification information will then be received by the computer, the calculation unit or the processor.

The user of the head-mounted device may then move to another position in the room, i.e. the second perspective, and may realign the virtual representation from the second viewing direction.

The consideration of the features that were found to a have a correct alignment from the first perspective during the displaying of the second overlap data in the second perspective ensures that the found well-alignment of said features is not neglected during further alignments of the virtual representation with the physical patient anatomy. For example, the alignment from the first perspective is shown as a picture-in-picture video or a screenshot when the second overlap data are displayed, i.e. when the user is watching the scene from the second perspective. The video content can for example be created with a previously, from the first perspective, recorded screenshot or video and can be combined with the virtual overlays. Another example of taking into account the alignment of the identified first area and/or anatomical feature of the patient anatomy during the displaying of the second overlap data is that a degree of freedom of a movability of the virtual representation is blocked, such that the user cannot move anymore the virtual representation along this degree of freedom.

In addition, analytical or numerical optimizations can be used in particular examples to calculate movements of the virtual representation that keep the identified first area/feature in the same alignment, or minimize a change of that alignment while at the same time bringing a second area/feature in alignment in the second perspective. In one particular example of taking into account the alignment identified in the first perspective, a numerical optimization is carried out, which calculates an optimized movement of the virtual representation. Such an optimized movement may minimize a change of the degree of alignment of the first area and/or of the first feature from the first perspective, while maintaining or maximizing the degree of alignment of the second area and/or of the second feature from the second perspective, as having at least a minimum degree of alignment. Another example is that the area and/or feature that was found to have a minimum degree of alignment from the first perspective, are then kept static when the virtual representation is realigned with the physical patient anatomy from the second perspective. Further details about such examples will be elucidated with and in the context of particular embodiments of the present invention hereinafter.

This beneficially ensures that the well alignment found from the first perspective, is not forgotten, but taken into account when the user continues the registration method in the next perspective. This leads to a fast converging registration method and the registration process can be finished much faster as compared to the prior art registration methods.

This method can be implemented and carried out by a medical system comprising e.g. a calculation unit, which is configured for carrying out the calculation steps described herein together with a head-mounted device for the user. This will be explained in more detail hereinafter.

In other words, the method registers iteratively a virtual representation of a patient anatomy with a coordinate system of a physical patient anatomy by matching a feature (i.e. the mentioned first area and/or first anatomical feature) in two or more perspectives of the user, wherein each perspective improves an accuracy of the registering. In each perspective, the feature is realigned in consideration of one or more alignments of one or more previous perspectives. This is efficient and accurate in comparison to point pair matching which requires more complex calculation operations as point pair matching requires a previous definition of a plurality points (i.e. predefined points) of the virtual representation and the physical patient anatomy and further a matching of all predefined points at once. Hence, the method simplifies the calculation process and at the same time increases the registering accuracy.

In certain embodiments, the virtual representation may be a volume model, a line model, a point model, or a surface model. It should be noted that the method does not require a modification (e.g. scaling, deforming etc.) of the virtual representation for registering. This may be efficient in terms of calculation effort. The method may only require a movement or displacement of the virtual representation in the coordinate system of the physical patient anatomy. The movement or displacement may comprise one or more of the six degrees of freedom. The virtual representation may be used to calculate a curve of a surface that may be used for registering.

According to another exemplary embodiment, the method does not use/require point pair matching for registering. Thus, the method presented does not predefine a plurality of points for the virtual representation and the physical anatomy of the patient in respective coordinate systems (i.e. coordinate system physical anatomy and coordinate system virtual representation), which are used for registering in point pair matching. This may be advantageous as point pair matching is very complex and time-consuming due to many necessary mathematical operations (e.g. deforming of the virtual representation in order to match single points, matching of the plurality of points, scaling of the virtual representation in order to match single points). Thus, as is understood by the skilled reader from the present disclosure, the method presented herein is different and in contrast to point pair matching for registering.

According to another exemplary embodiment, the first area and/or anatomical feature of the first overlap data and second overlap data is/are used for registering instead of point pair matching. Instead of a plurality of predefined points the method uses merely overlap data from two or more different perspectives. Theses overlap data are derived from the different perspectives of the user. The different perspectives can be understood as respective snapshots. Hence, the calculation effort may advantageously decrease due to a reduction of necessary matching operations as for example only two areas and/or anatomical features in two different perspectives have to be matched instead of a plurality of predefined points.

According to another exemplary embodiment, the method is carried out without a marker and/or a predefined landmark. In other words, the present invention is a marker-less method and/or a landmark-less method for registering a virtual representation of a patient anatomy with a coordinate system of a physical patient anatomy. This may be advantageous as it increases an efficiency of the registering due the absence/abandonment of the marker and/or the landmark. Further, this may be advantageous in terms of flexibility, as predefined landmarks may not fit to a broad variety of humans equally good. E.g., a predefined landmark is a cheekbone, but the cheekbone of one or more patients may not be strongly developed and therefore not easy to match. Hence, it is advantageous to identify a first area and/or a first anatomical feature during the method and maintain all possibilities for identifying them instead of a prior definition of the landmark. In this way, the method can address most of the anatomical differences by humans.

According to another exemplary embodiment, the method is carried without a pointer-assisted definition of landmarks on the anatomy of the patient.

According to an exemplary embodiment, the first area and/or the anatomical feature is identified by the user and/or by image processing during the method. This means that the anatomical feature is not predefined. The first area and/or anatomical feature may be described by one or more edges or a contour that are clearly visible. This visibility may vary from patient to patient. Hence, it is advantageous that the user and/or image processing identify the first area and/or the anatomical feature.

According to an exemplary embodiment, the alignment of the identified first area and/or anatomical feature of the patient anatomy that was identified in the first visual overlap constrains an alignment of the identified first area and/or anatomical feature of the patient anatomy in the second visual overlap. In other words, the registering in the present case is an iterative process wherein each iteration (i.e. further perspective) affects the registering. Each further perspective serves as further condition for registering. This is advantageous as an accuracy of the registering may increase although only a reduced calculation effort is necessary as no time consuming point matching is carried out. Hence, the method may advantageously be very efficient.

According to an exemplary embodiment of the invention, the method comprises:

e) receiving a user input signal describing a movement of the virtual representation of the patient anatomy relative to the physical patient anatomy initiated by a user of the head-mounted device in the second perspective (step S5), f) calculating a change of the degree of the alignment of the identified first area and/or of the first anatomical feature of the patient anatomy caused by the movement of the virtual representation of the patient anatomy relative to the physical patient anatomy initiated by the user in the second perspective (step S6), and g) using the calculated change of the degree of alignment of the identified first area and/or of the first anatomical feature of the patient anatomy for the displaying of the second overlap data (step S7).

The step of receiving a user input signal describing the movement of the virtual representation may be triggered by moving the virtual representation in space and placing it on the patient anatomy by the user using a control means like e.g. a joystick. This user input signal is received by a computer/calculation unit carrying out the method presented herein. It is then calculated how the impact caused by this movement on the degree of alignment of the previously identified first area and/or first anatomical feature is or would be. This calculated change of the degree of alignment of the identified first area and/or of the first anatomical feature is then used for the displaying of the second overlap data.

For example, a graphical indicator may be displayed to the user when he/she is in the second perspective, which indicates and shows to the him/her how much the first alignment of the first identified area/feature changes when the movement that was caused by the user is indeed carried out for the virtual representation. In another example, using the calculated change of the degree of alignment of the identified first area and/or of the first anatomical feature is embodied as applying a restriction of the movability of the virtual representation in the mixed reality seen by the user. Since the virtual representation can then not be moved any further, beyond for example a particular plane, this is considered to use the calculated change for the displaying of the second overlap data, since the second overlap data are restricted based on the change of degree of alignment. This will be explained in more detail in the context of further embodiments hereinafter.

According to another exemplary embodiment of the invention, the method comprises the step of calculating the second overlap data and minimizing, during the calculation of the second overlap data, the change of degree of the alignment of the identified first area and/or of the first anatomical feature of the patient anatomy.

In other words, in this embodiment, the method minimizes the impact of the desired movement initiated by the user onto the alignment of the identified first area and/or identified first anatomical feature when calculating the second overlap data. Thus, based on the user input, the method may calculate an optimal solution for keeping the identified well-aligned features in the same or nearly the same alignment, as well as proceeding with the movement of the virtual representation as initiated by the user of the head-mounted device when he is in the second perspective. A more detailed embodiment carrying out an optimization algorithm will be described hereinafter in detail.

According to another exemplary embodiment of the present invention, the method comprises the step of:
j) generating a control signal for the head-mounted device,
   wherein the control signal is configured for ensuring that the second visual overlap is only displayed to the user in the second perspective in case the alignment between the virtual representation and the physical patient anatomy of the identified first area and/or identified first anatomical feature does not change more than a pre-defined threshold value.

In this embodiment, the user may previously define a threshold value how much the alignment of the features that were identified to have a correct alignment from the first perspective may change during a realignment of the visual representation from the second perspective. The generated control signal may then restrict the movability of the virtual representation when the user triggers such a movement by for example a joystick or another appropriate control means of the corresponding medical system.

According to another exemplary embodiment of the present invention, the identified first area and/or the identified first anatomical feature of the patient anatomy are kept static during a realignment of the virtual representation of the patient anatomy and the physical patient anatomy by the user from the second perspective.

If for example the virtual nose, which is part of the virtual representation, is matched exactly with the patient's nose from the first perspective, the nose is defined as having a correct alignment. When realigning the virtual representation from the second perspective, the axis from the head-mounted device in the first perspective through the nose remains static, i.e. fixed, which will be understood by the skilled reader as a constraint of the movability of the virtual representation in the mixed reality.

According to another exemplary embodiment of the present invention, the method comprises blocking at least one degree of freedom out of three translational degrees of freedom and three rotational degrees of freedom of a movability of the virtual representation of the patient anatomy when the user is in the second perspective.

Based on the identified at least first area/anatomical feature in the first visual overlap, the at least one degree of freedom to be blocked can be determined. An example of such a restriction of the movability of the virtual representation has been given herein before with respect to the virtual nose that is matched exactly with the patient's nose in the first perspective. In this example, the axis from the head-mounted device in the first viewing direction through the nose was kept fixed and therefore, one degree of freedom of the movability of the virtual representation was blocked.

According to another exemplary embodiment, a feedback signal for the user is generated, which informs the user about the at least one blocked degree of freedom and/or about non-blocked degrees of freedom for initiating a movement of the virtual representation of the patient anatomy relative to the physical patient anatomy in the second perspective.

In other words, the user is informed with this feedback signal that particular constraints for the movability of the virtual representation have been calculated and implemented by the presented embodiment. Various different graphical elements and graphical functionalities may be used to show the user, which degree of freedom is blocked and/or which degree of freedom is not blocked. This provides guidance for the user in the registration process is doing in the mixed reality that he sees through the head-mounted device.

According to another exemplary embodiment of the present invention, the method suggests at least one perspective for the user based on blocked and/or non-blocked degrees of freedom.

In this way the user is provided with a suggestion into which position and/or perspective he shall move with the head-mounted device for the next realignment of the visual representation with the physical patient anatomy. This calculated suggestion may be displayed to the user on the display of the head-mounted device, such that the user can move towards the suggested area or suggested perspective. The suggestion may take into account an appropriate and proper perspective, such that the user can efficiently and fast align the virtual representation with the patient anatomy without causing a too high impact on the features that were found to be well-aligned from the first perspective.

According to another exemplary embodiment of the present invention, the method comprises the step of determining a constraint of the virtual representation of the patient anatomy relative to the physical patient anatomy based on the identified first area and/or of the identified first anatomical feature of the patient anatomy. The method also comprises using the determined constraint for generating a control signal for the head-mounted device. The method further comprises the step of restricting the movability of the virtual representation of the patient anatomy displayed to the user in the head-mounted device based on the determined constraint.

In an example, such a constraint may be a fixed point and/or a fixed axis, as has been described herein before in the context of another embodiment. The correct alignment that was identified from the first perspective can lead to situations where the virtual representation shall not be movable in such a way that the alignment between the virtual representation and the physical patient anatomy is not allowed to change for this fixed point and/or for this fixed axis.

According to another exemplary embodiment of the present invention, the step S2, i.e. identifying the first area and/or the first anatomical feature of the patient anatomy having the at least minimum degree of alignment between the virtual representation and the physical patient anatomy comprises:

q) detecting a visual overlap of at least one corresponding edge of the virtual representation and of the physical patient anatomy, detecting a visual overlap of at least one corresponding contour of the virtual representation and of the physical patient anatomy, and/or detecting a visual overlap of at least one corresponding visual gradient of the virtual representation and of the physical patient anatomy (step S2a).

Generally, this detection may be carried out manually by a user, but may also be carried out by a corresponding algorithm, i.e. being a computer-implemented medical method step. The person skilled in the art will know, based on this disclosure and his knowledge, how to implement an automatic detection of corresponding contours, corresponding edges and/or correspondent visual gradients. Since this detection happens in a mixed reality, i.e. where the virtual representation is overlaid over the real patient's body, detecting corresponding edges, corresponding contours and/or corresponding visual gradients automatically, will result in a reliable and fast method of identifying the first area/anatomical feature having an least minimum degree of alignment.

According to another exemplary embodiment of the present invention, the method comprises the automatic detection that the user has moved from the first perspective into the second perspective.

In an example, this automatic detection can be carried out by tracking, preferably by using an optical tracking system, the head-mounted device relative to its surrounding. In this way, the computer and/or system carrying out the method presented herein will know that the user is in the second perspective and will soon initiate a movement of the virtual representation of the patient anatomy relative to the physical patient anatomy.

According to another exemplary embodiment, the method comprises the step of changing coordinates of the virtual representation of the patient anatomy within the coordinate system of the physical patient anatomy by moving the displayed virtual representation relative to the physical patient anatomy by a user of the head-mounted device.

In other words, this embodiment describes that the coordinates of the model are changed in the coordinate system of the anatomy when the model is moved by the user in the control mode of the medical system carrying out the presented registration method. Thus, the control mode is not the final mode of using the mixed reality, in which the virtual representation is spatially fixed, such that the virtual representation and its position and orientation is adapted when the user is moving. In the control mode, the virtual representation is not spatially fixed and the user can, by moving the spatial representation, change its coordinates in the coordinate system of the physical patient anatomy.

According to another exemplary embodiment of the present invention, the method comprises:

t) receiving a user input signal describing a movement of the virtual representation of the patient anatomy relative to the physical patient anatomy initiated by a user of the head-mounted device in the second perspective, and u) generating a control signal for the head-mounted display for displaying the movement of the virtual representation of the patient anatomy relative to the physical patient anatomy in a display of the head-mounted device.

Such a user input signal can be generated, for example, by a user control means, which can exemplarily be embodied as for example a joystick. With this user control means, the user specifies a desired movement of the virtual representation of the patient anatomy relative to the physical patient anatomy. An exemplary embodiment thereof can be seen from FIG. 2 and its description.

According to another exemplary embodiment of the present invention, the method comprises:

v) receiving a user input signal describing a movement of the virtual representation of the patient anatomy relative to the physical patient anatomy initiated by a user of the head-mounted device in the second perspective (S9), w) identifying at least a second area in the second visual overlap and/or at least a second anatomical feature of the patient anatomy in the second visual overlap having at least a minimum degree of alignment between the virtual representation and the physical patient anatomy (S10), x) carrying out a numerical optimization, which calculates an optimized movement of the virtual representation of the patient anatomy relative to the physical patient anatomy (S11), and wherein the optimized movement minimizes a change of the degree of alignment of the first area and/or of the first feature from the first perspective while maintaining or maximizing the degree of alignment of the second area and/or of the second feature from the second perspective between the virtual representation of the patient anatomy and the physical patient anatomy.

This embodiment describes that a user moves the model when he/she is in the second perspective and also that a second area/feature is identified, for which a good alignment, i.e. a high correlation or congruency, is achieved. Based on the "suggested movement" caused by the user and the identified second area/feature, a numerical optimization is carried out looking for "better movements".

In other words, this embodiment optimizes the realignment of the virtual representation with the physical patient anatomy while ensuring that the impact of the realignment from the second perspective onto the previously identified well-alignment of the identified first area and/or first anatomical feature is minimized. An optimization algorithm may be used that takes into account both targets. First, the movement to be calculated shall maintain or maximize the degree of alignment of the second area and/or of the second feature from the second perspective. On the other hand, the movement to be calculated shall minimize a change of the degree of alignment of the first area and/or of the first feature from the first perspective.

According to another exemplary embodiment of the present invention, the method comprises displaying the second overlap data in the head-mounted device from the second perspective thereby transparently displaying to the user at least one area and/or at least one feature of the virtual representation of the patient anatomy, which prevents a direct view from the second perspective onto the identified first area and/or the identified first anatomical feature of the patient anatomy having the at least minimum degree of alignment.

In other words, with this embodiment, a transparent illustration of areas of the virtual representation is used, which areas would prevent that the user directly sees the first region and/or the first anatomical feature that were previously identified to be well-aligned when seen from the first perspective. In other words, a so-called x-ray view of that areas of the virtual representation, which block or prevent the direct view of the user to said area and/or feature that were previously identified as being well-aligned, is used in this embodiment. This guides the user through the registration process and leads to a fast converging registration process.

According to another exemplary embodiment of the present invention, the method comprises the step of displaying the second overlap data in the head-mounted device thereby also displaying a first perspective deviation indicator to the user. The first perspective deviation indicator indicates an alignment or misalignment between the virtual representation and the physical patient anatomy for the identified first area/anatomical feature of the patient anatomy to the user in the mixed reality. Moreover, this alignment or misalignment is caused by a user input from the second perspective for moving the virtual representation relative to the physical patient anatomy.

In particular when the first and the second perspectives are orthogonal to each other, this embodiment may be of particular advantage. The changes of the alignment of the features that were identified in the first perspective to be well-aligned, due to the movement of the virtual representation by the user when he/she is in the second perspective, can be in this way made visible to the user. For example, a displayed number/index indicating the degree of alignment or misalignment may be displayed to the user in the head-mounted device. However, also other graphical means like a colour code may be used to indicate to the user the value of alignment or misalignment. This guides the user through the registration process and leads to a fast converging registration process.

According to another exemplary embodiment of the present invention, the method comprises the step of recording, from the first perspective, an image and/or a video of the displayed first overlap data and displaying the recorded image and/or video in the head-mounted device while the user is in the second perspective and while the second overlap data are displayed to the user in the head-mounted device.

In other words, this embodiment relates to the picture-in-picture video solution and describes a particular way of implementing the feature of taking into account, during the displaying of the second overlap data, the alignment of the identified first area/anatomical feature of the patient anatomy that was identified in the first perspective to have a proper alignment.

According to another exemplary embodiment of the present invention, the method comprises the step of providing sensor image data of at least one sensor within the head-mounted device, wherein the sensor image data depict from the first perspective the first visual overlap between the virtual representation of the patient anatomy and the physical patient anatomy. Therein, the identification of the first area and/or the first anatomical feature of the patient anatomy having the at least minimum degree of alignment (step S2) comprises the step of comparing the provided sensor image data with the virtual representation of the patient anatomy thereby automatically identifying the first area and/or the first anatomical feature of the patient anatomy having the at least minimum degree of alignment between the virtual representation and the physical patient anatomy.

By using the sensor positioned within the head-mounted device, the automatic detection of the features, which are in alignment, can be carried out. In this way, it can be avoided that the user needs to find corresponding edges, contours and/or visual gradients in the virtual overlay that he sees in the head-mounted device.

According to another exemplary embodiment of the present invention, the method comprises the step of determining six degrees of freedom of the movability of the virtual representation of the patient anatomy, wherein the six degrees of freedom are three translational degrees of freedom and three rotational degrees of freedom.

In other words, the method as presented herein may be repeated as often as desired by the user and the user may make use of not only the first and the second perspective, but may use a third, a fourth, and even more perspectives until he is satisfied with the alignment of the virtual representation and the physical patient anatomy. When the method is completed, the registration of the virtual representation within the coordinate system of the physical patient anatomy is completed, and at this point, the six degrees of freedom of the movability of the virtual representation have been determined.

According to a second aspect of the present invention, a program is presented which, when running on a computer or when loaded onto a computer, causes the computer to perform the method steps of the method according to any one of the preceding claims; and/or a program storage medium on which the program is stored; and/or a computer comprising at least one processor and a memory and/or the program storage medium, wherein the program is running on the computer or loaded into the memory of the computer; and/or a signal wave or a digital signal wave, carrying information which represents the program; and/or a data stream which is representative of the program.

According to a third aspect of the present invention, a medical system for registering a virtual representation of a patient anatomy with a coordinate system of a physical patient anatomy is presented. The medical system comprising a calculation unit,
wherein the calculation unit is configured for
causing a displaying of first overlap data in a head-mounted device, wherein the first overlap data describe from a first perspective onto the physical patient anatomy a first visual overlap between the virtual representation of the patient anatomy and the physical patient anatomy,
identifying at least a first area in the first visual overlap and/or at least a first anatomical feature of the patient anatomy in the first visual overlap having at least a minimum degree of alignment between the virtual representation and the physical patient anatomy, and
displaying second overlap data in the head-mounted device, wherein the second overlap data describe from a second perspective onto the physical patient anatomy a second visual overlap between the virtual representation of the patient anatomy and the physical patient anatomy, and taking into account, during the displaying of the second overlap data, the alignment of the identified first area and/or anatomical feature of the patient anatomy that was identified in the first visual overlap as having at least a minimum degree of alignment between the virtual representation and the physical patient anatomy (step S4).

According to an exemplary embodiment of the present invention, the medical system further comprises a head-mounted device for displaying the first and second overlap data to the user.

Moreover, it is emphasized that features, functions, elements and/or steps, which are described above and in the following with reference to one aspect of the invention, equally apply to any other aspect of the invention described above and in the following. Particularly, features and/or steps, as described above and in the following with reference to the method according to the first aspect equally apply to the computer program, to the computer-readable medium, to the computer and to the medical system, and vice versa.

These and other aspects of the invention will become apparent from and elucidated with reference to the embodiments described hereinafter.

Definitions

In this section, definitions for a specific terminology used in this disclosure are offered which also form part of the present disclosure.

Computer Implemented Method

The method in accordance with the invention is for example a computer implemented method. For example, all the steps or merely some of the steps (i.e. less than the total number of steps) of the method in accordance with the invention can be executed by a computer (for example, at least one computer). An embodiment of the computer implemented method is a use of the computer for performing a data processing method. An embodiment of the computer implemented method is a method concerning the operation of the computer such that the computer is operated to perform one, more or all steps of the method.

The computer for example comprises at least one processor and for example at least one memory in order to (technically) process the data, for example electronically and/or optically. The processor being for example made of a substance or composition which is a semiconductor, for example at least partly n- and/or p-doped semiconductor, for example at least one of II-, III-, IV-, V-, VI-semiconductor material, for example (doped) silicon and/or gallium arsenide. The calculating or determining steps described are for example performed by a computer. Determining steps or calculating steps are for example steps of determining data within the framework of the technical method, for example within the framework of a program. A computer is for example any kind of data processing device, for example electronic data processing device. A computer can be a device which is generally thought of as such, for example desktop PCs, notebooks, netbooks, etc., but can also be any programmable apparatus, such as for example a mobile phone or an embedded processor. A computer can for example comprise a system (network) of "sub-computers", wherein each sub-computer represents a computer in its own right. The term "computer" includes a cloud computer, for example a cloud server. The term "cloud computer" includes a cloud computer system which for example comprises a system of at least one cloud computer and for example a plurality of operatively interconnected cloud computers such as a server farm. Such a cloud computer is preferably connected to a wide area network such as the world wide web (WWW) and located in a so-called cloud of computers which are all connected to the world wide web. Such an infrastructure is used for "cloud computing", which describes computation, software, data access and storage services which do not require the end user to know the physical location and/or configuration of the computer delivering a specific service. For example, the term "cloud" is used in this respect as a metaphor for the Internet (world wide web). For example, the cloud provides computing infrastructure as a service (IaaS). The cloud computer can function as a virtual host for an operating system and/or data processing application which is used to execute the method of the invention. The cloud computer is for example an elastic compute cloud (EC2) as provided by Amazon Web Services™. A computer for example comprises interfaces in order to receive or output data and/or perform an analogue-to-digital conversion. The data are for example data which represent physical properties and/or which are generated from technical signals. The technical signals are for example generated by means of (technical) detection devices (such as for example devices for detecting marker devices) and/or (technical) analytical devices (such as for example devices for performing (medical) imaging methods), wherein the technical signals are for example electrical or optical signals. The technical signals for example represent the data received or outputted by the computer. The computer is preferably operatively coupled to a display device which allows information outputted by the computer to be displayed, for example to a user.

One example of a display device is a head-mounted device as used herein, i.e. a virtual reality device or an augmented reality device (also referred to as virtual reality glasses or augmented reality glasses) which can be used as "goggles" for navigating. A specific example of such augmented reality glasses is Google Glass (a trademark of Google, Inc.). An augmented reality device or a virtual reality device can be used both to input information into the computer by user interaction and to display information outputted by the computer. Another example of a display device would be a standard computer monitor comprising for example a liquid crystal display operatively coupled to the computer for receiving display control data from the computer for generating signals used to display image information content on the display device. A specific embodiment of such a computer monitor is a digital lightbox. An example of such a digital lightbox is Buzz®, a product of Brainlab AG. The monitor may also be the monitor of a portable, for example handheld, device such as a smart phone or personal digital assistant or digital media player.

The invention also relates to a program which, when running on a computer, causes the computer to perform one or more or all of the method steps described herein and/or to a program storage medium on which the program is stored (in particular in a non-transitory form) and/or to a computer comprising said program storage medium and/or to a (physical, for example electrical, for example technically generated) signal wave, for example a digital signal wave, carrying information which represents the program, for example the aforementioned program, which for example comprises code means which are adapted to perform any or all of the method steps described herein.

Within the framework of the invention, computer program elements can be embodied by hardware and/or software (this includes firmware, resident software, micro-code, etc.). Within the framework of the invention, computer program elements can take the form of a computer program product which can be embodied by a computer-usable, for example computer-readable data storage medium comprising computer-usable, for example computer-readable program instructions, "code" or a "computer program" embodied in said data storage medium for use on or in connection with the instruction-executing system. Such a system can be a computer; a computer can be a data processing device comprising means for executing the computer program elements and/or the program in accordance with the invention, for example a data processing device comprising a digital processor (central processing unit or CPU) which executes the computer program elements, and optionally a volatile memory (for example a random access memory or RAM) for storing data used for and/or produced by executing the computer program elements. Within the framework of the present invention, a computer-usable, for example computer-readable data storage medium can be any data storage medium which can include, store, communicate, propagate or transport the program for use on or in connection with the instruction-executing system, apparatus or device. The computer-usable, for example computer-readable data storage medium can for example be, but is not limited to, an electronic, magnetic, optical, electromagnetic, infrared or semiconductor system, apparatus or device or a medium of propagation such as for example the Internet. The computer-usable or computer-readable data storage medium could even for example be paper or another suitable medium onto which the program is printed, since the program could be electronically captured, for example by optically scanning the paper or other suitable medium, and then compiled, interpreted or otherwise processed in a suitable manner. The data storage medium is preferably a non-volatile data storage medium. The computer program product and any software and/or hardware described here form the various means for performing the functions of the invention in the example embodiments. The computer and/or data processing device can for example include a guidance information device which includes means for outputting guidance information. The guidance information can be outputted, for example to a user, visually by a visual indicating means (for example, a monitor and/or a lamp) and/or acoustically by an acoustic indicating means (for example, a loudspeaker and/or a digital speech output device) and/or tactilely by a tactile indicating means (for example, a vibrating element or a vibration element incorporated into an instrument). For the purpose of this document, a computer is a technical computer which for example comprises technical, for example tangible components, for example mechanical and/or electronic components. Any device mentioned as such in this document is a technical and for example tangible device.

BRIEF DESCRIPTION OF THE DRAWINGS

In the following, the invention is described with reference to the appended Figures, which give background explanations and represent exemplary embodiments of the invention. The scope of the invention is, however, not limited to the specific features disclosed in the context of the features, wherein FIG. 1 schematically shows first overlap data seen from a user in a head-mounted device, wherein the first overlap data describe from a first perspective onto the physical patient anatomy a first visual overlap between a virtual representation of the patient anatomy and the physical patient anatomy, as used in exemplary embodiments of the present invention, FIG. 2 schematically shows a medical system for registering a virtual representation of a patient anatomy with a coordinate system of a physical patient anatomy according to an exemplary embodiment of the present invention.

The Figures are schematically only and not true to scale. In principle, identical or like parts, elements and/or steps are provided with identical or like reference symbols in the Figures.

DESCRIPTION OF EMBODIMENTS

Figure 1:
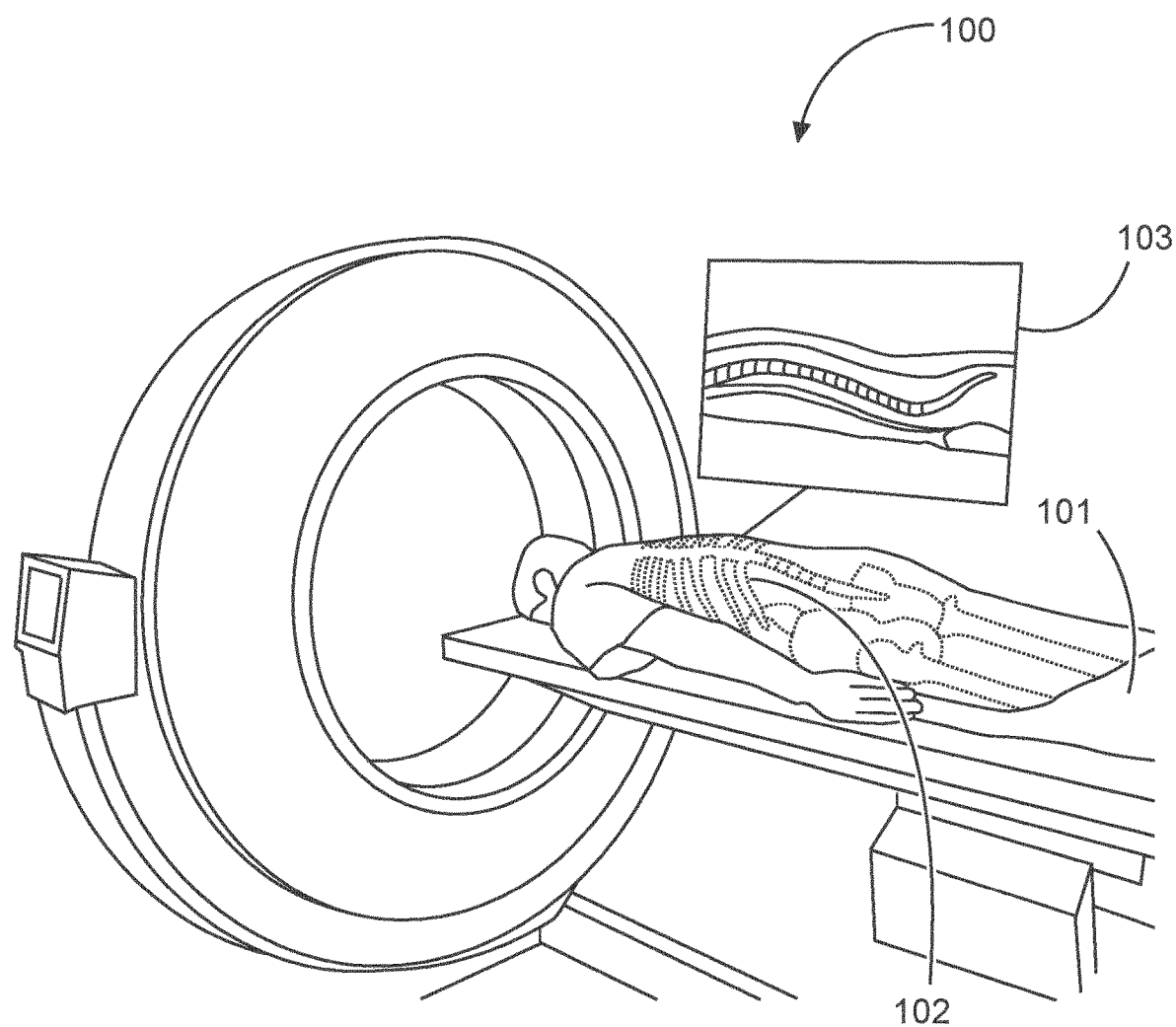

FIG. 1 shows a medical scene 100 seen through a head-mounted device (see e.g. mixed reality goggles 202 in FIG. 2), in which mixed reality or augmented reality is used for registering a virtual representation of a patient anatomy with a coordinate system of a physical patient anatomy. As can be seen from FIG. 1, a patient 101 is laying on a patient support for being moved into a medical imaging system. The patient 101 can be seen as the physical patient anatomy as described herein. FIG. 1 further shows a virtual representation of the patient anatomy, which is shown in FIG. 1 with reference sign 102. Alternatively or in addition, medical planning data could be shown which need to be registered as well. FIG. 1 thus represents the view out of a head-mounted device in which first overlap data are displayed to the user of the head-mounted device. The first overlap data describe from a particular first perspective, in which the user is currently standing, a first visual overlap between the virtual representation of the patient anatomy 102 and the real patient, i.e. the physical patient anatomy 101.

In addition, display 103 shows a cross-sectional view through the virtual representation of the patient anatomy 102 such that the user is provided with additional information. The general concept of this graphic is that information presented in the mixed reality experience can both be information overlaid at its natural position as well as artificial information that does not correspond to reality presented or to the current viewing orientation in kind of a virtual screen. For example, in spinal surgery it might be advantageous to review an axial view of the spine when placing a pedicle screw although the surgeon is standing at the side of the table and does not naturally look along the central axis of the body. This feature of displaying such additional information is of course also part of an exemplary embodiment of the present invention.

Figure 2:
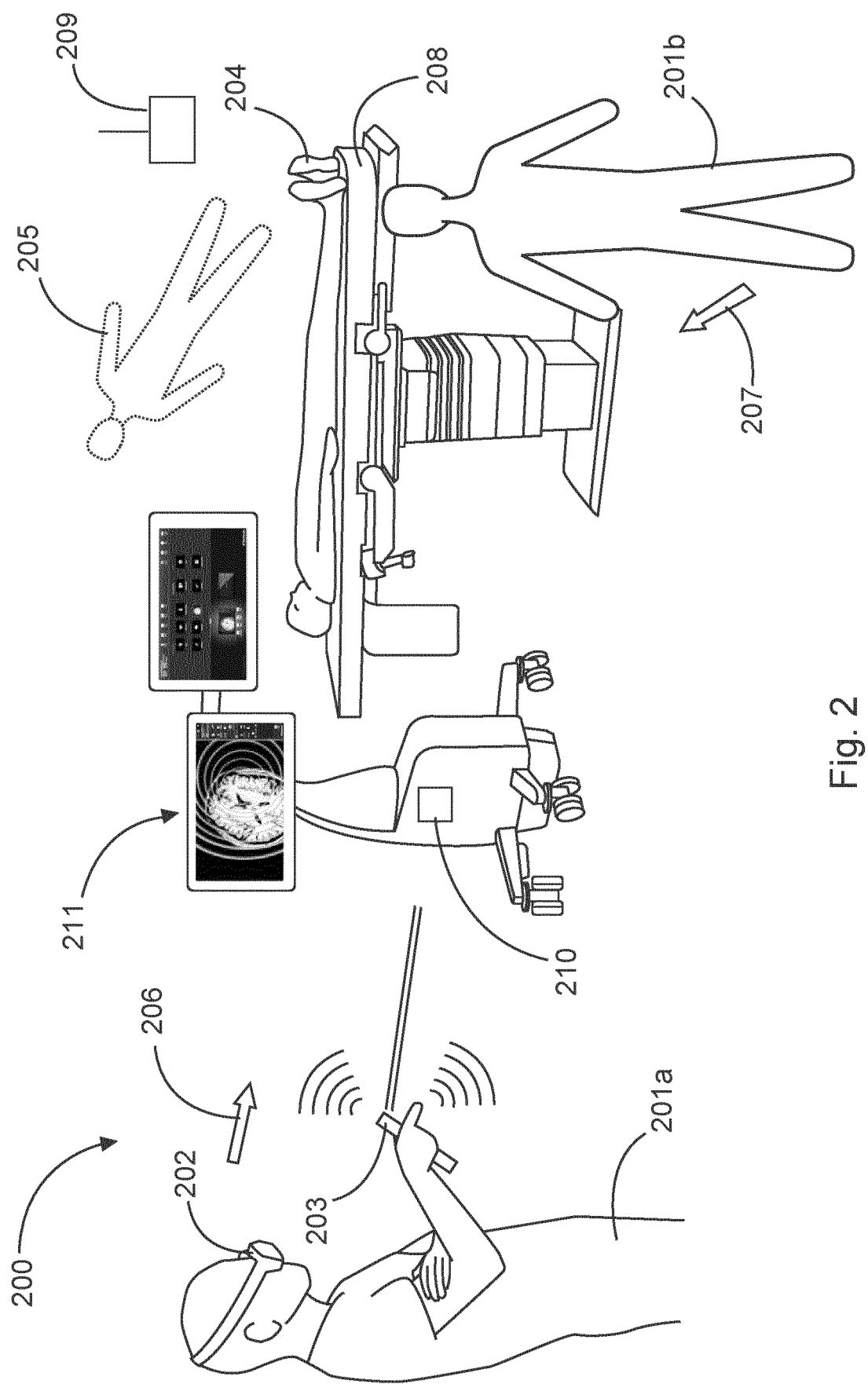

FIG. 2 schematically shows a medical system 200 for registering a virtual representation of a patient anatomy 205 with a coordinate system (not shown here) of the physical patient anatomy 204. The medical system 200 comprises a calculation unit 210 for carrying out particular steps as described herein before and hereinafter in detail, wherein the calculation unit 210 is exemplarily integrated herein in mobile station 211. The user 201a, 201b holds a user control means 203, i.e. a joystick, in his hands, with which he can generate a user input signal to move the virtual representation of a patient anatomy 205 within the coordinate system of anatomy 204. Note that the presented system 200 and the corresponding method can also involve a plurality of users, each wearing such a head-mounted device 202. This allows a collective registration by the plurality of users. For example, a first user may identify the first area/feature from the first perspective and a second user may identify the second area/feature from the second perspective.

The medical system 200 is in this scenario in the control mode, in which the coordinates of the virtual representation are changed in the coordinate system of the anatomy when the model is moved by the user. The control mode is not the final mode of using the mixed reality, in which the virtual representation is spatially fixed, such that the virtual representation and its position and orientation is adapting accordingly when the user is moving. In the control mode, the virtual representation is not spatially fixed and the user can, by moving the spatial representation, change its coordinates in the coordinate system of the physical patient anatomy for carrying out the registration. Thus, the user control means 203 allows the user to specify a desired movement of the virtual representation 205 relative to the physical patient anatomy 204 in the displayed first visual overlap that the user sees in the head-mounted device 202.

FIG. 2 further shows an optical tracking system 209 for automatically detecting the head-mounted device 202 when it is moving in the room together with the user 201a, 201b. The user 201a viewing the patient anatomy 204 from the first perspective 206 can identify, e.g. with the control means 203, the areas and/or the anatomical features in the patient anatomy in said first visual overlap, which has a correct alignment, i.e. the aforementioned at least a minimum degree of alignment between the virtual representation and the physical patient anatomy. This identification of a well-aligned area and/or a well-aligned anatomical feature can be done manually by the user 201a, e.g. by manually marking or highlighting the correctly aligned area/feature in the displayed visual overlap, i.e. in the mixed reality, with the control means 203. Alternatively, this can be done automatically by calculation unit 210 and e.g. at least one sensor within the head-mounted device. Such a sensor creates sensor image data depicting from the first perspective 206 the first visual overlap between the virtual representation and the physical patient anatomy. Therein, the identification of the first area and/or the first anatomical feature of the patient anatomy having the at least minimum degree of alignment (step S2 of FIG. 3) is carried out by comparing the sensor image data with the virtual representation of the patient anatomy. This allows an automatic identification of the first area and/or the first anatomical feature of the patient anatomy having the at least minimum degree of alignment between the virtual representation and the physical patient anatomy by the calculation unit 210. By using the sensor (not shown here) positioned within the head-mounted device 202, the automatic detection of the features, which are in alignment, can be carried out. In a particular embodiment, the calculation unit 210 is configured for detecting a visual overlap of at least one corresponding edge of the virtual representation and of the physical patient anatomy, the calculation unit is configured for detecting a visual overlap of at least one corresponding contour of the virtual representation and of the physical patient anatomy, and/or the calculation unit is configured for detecting a visual overlap of at least one corresponding visual gradient of the virtual representation and of the physical patient anatomy. In this way, it can be avoided that the user needs to find corresponding edges, contours and/or visual gradients in the virtual overlay that he sees in the head-mounted device.

It is clear that after having moved into the second perspective 207, user 201b can see the mixed reality from this second perspective and can do a realignment of the virtual representation. When being in the second perspective 207, second overlap data are displayed in the head-mounted device. The second overlap data describe from perspective 207 a second visual overlap between the virtual representation 205 of the patient anatomy and the physical patient anatomy 204. The method and system of the embodiment shown in FIG. 2 take into account, during the displaying of the second overlap data, the alignment of the identified first area and/or anatomical feature of the patient anatomy that was identified from the perspective 206 as having a correct alignment between the virtual representation 205 and the physical patient anatomy 204.

The consideration of the features that were found to a have a correct alignment when seen from the first perspective 206 during the displaying of the second overlap data in the second perspective 207 ensures that the found correct alignment of said features is not neglected during further alignments of the registration from e.g. perspective 207. In one example, the alignment from the first perspective 206 is shown as a picture-in-picture video or a screenshot in the head-mounted device 202 when the second overlap data are displayed, i.e. when the user is watching the scene from the second perspective 207. The video content can, for example, be created with a previously, from the first perspective 206, recorded screenshot or video and can be combined with the virtual overlays in the head-mounted device 202.

It should be noted here that the virtual representation of a patient anatomy may be a volume model and that the virtual representation of the patient anatomy is merely moved and not deformed. Further, it should be noted that the method does not predefine any points in the virtual representation of the patient anatomy 205 nor in the physical patient anatomy 204 in order to carry out the registering of the virtual representation of the patient anatomy 205 with a coordinate system of the physical patient anatomy 204. Instead, the method as described above uses the alignment of the first perspective 206 and the realignment of the second perspective 207. As described above the alignment in the first perspective 206 may be carried out e.g. by detecting a visual overlap of at least one corresponding edge of the virtual representation and of the physical patient anatomy. The realignment in the second perspective 207 considers further the alignment of the first perspective 206. Hence, the method does not pursue a point pair matching or the like. The method enables an iterative alignment of the virtual representation of the patient anatomy 205 with a coordinate system of the physical patient anatomy 204.

Another example of taking into account the alignment of the identified first area and/or anatomical feature during the displaying of the second overlap data is that a degree of freedom of a movability of the virtual representation 205 is blocked, i.e. constrained. In this way, the user 201b cannot move anymore the virtual representation 205 along this degree of freedom when using control means 203 for doing realignments for completing the registration process.

In addition, analytical or numerical optimizations can be carried out on the calculation unit 210 to calculate movements of the virtual representation that keep the identified first area/feature in the same alignment, or minimize a change of that alignment while at the same time bringing a second area/feature in alignment in the second perspective.

Yet another example of taking into account the alignment identified in the first perspective is carrying out a numerical optimization by calculation unit 210, which calculates an optimized movement of the virtual representation in the second perspective 207. Such an optimized movement may minimize a change of the degree of alignment of the first area and/or of the first feature from the first perspective 206, while maintaining or maximizing the degree of alignment of the second area and/or of the second feature from the second perspective, as having at least a minimum degree of alignment. Yet another example is that the area and/or feature that was found to have a minimum degree of alignment from the first perspective are then kept static by the calculation device 210 when the virtual representation 205 is realigned with the physical patient anatomy 204 from the second perspective 207. It is kindly referred to the practical example about matching the nose of a patient with the model, discussed in detail hereinbefore.

The medical system 200 for registering the virtual representation of the patient anatomy 205 with a coordinate system (not shown here) of the physical patient anatomy 204, advantageously reduces the number of perspectives needed for the registration. This holds true due to the consideration of the alignment of the identified first area/first feature that was found to be correct from the first perspective 206, when displaying the second visual overlay from the second perspective 207. In another particular embodiment, the calculation unit 210 is configured for taking into account the change of and/or the impact on the alignment of the identified first area/feature (identified from the first perspective 206) due to a movement of the virtual representation desired/triggered by the user when realigning the visual representation and the physical patient anatomy from the second perspective 207.

As is apparent to the skilled reader, the system 200 shown in FIG. 2 can also be programmed and configured to carry out the method embodiments that will be explained in detail in the context of FIGS. 3 to 5 now.

Figure 3:
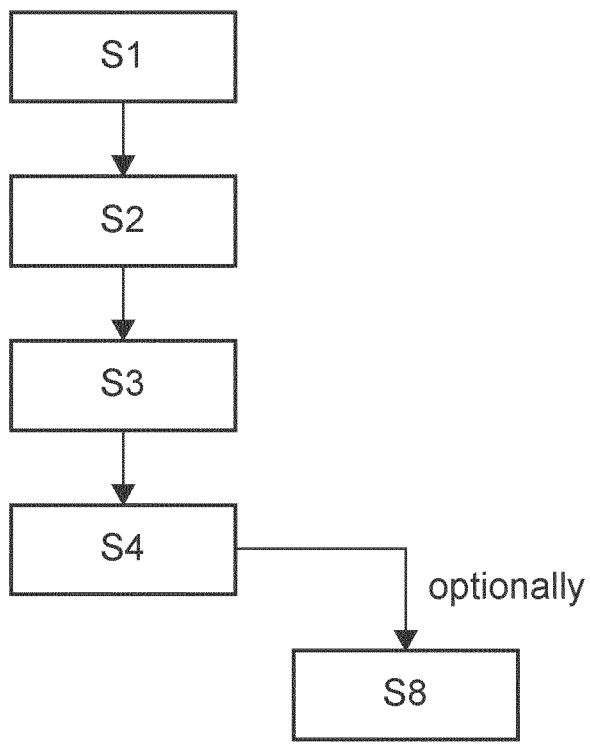
FIG. 3 shows a flow diagram of a method for registering a virtual representation of a patient anatomy with a coordinate system of a physical patient anatomy according to an exemplary embodiment of the present invention.

In particular, FIG. 3 discloses a flow diagram of a method for registering a virtual representation of a patient anatomy with a coordinate system of a physical patient anatomy. The method as presented herein sets out in the context of head-mounted mixed reality systems, where virtual representations of an anatomy or planning data are overlaid above a real, physical patient anatomy. The process of registering such a virtual representation of a patient anatomy with a coordinate system of a physical patient anatomy involves that the user aligns the virtual representation and the anatomy from at least two different perspectives by manually moving the virtual representation into the, at least from this perspective, correct and well-aligned position. The user may thus initiate several times a movement of the virtual representation relative to the physical patient anatomy, for example by using a joystick or another user control means. Such a control means with which the user triggers and/or specifies the desired movement of the virtual representation relative to the physical patient anatomy can be seen in for example the embodiment described in the context of FIG. 2. When the user is satisfied with the alignments of the virtual representation and the physical patient anatomy from two or more perspectives, he completes the registration process.

Thus, the method shown in FIG. 3 comprises displaying first overlap data in a head-mounted device, wherein the first overlap data describe from a first perspective onto the physical patient anatomy a first visual overlap between the virtual representation of the patient anatomy and the physical patient anatomy, i.e. step S1. The method of FIG. 3 also comprises the step of identifying at least a first area in the first visual overlap and/or at least a first anatomical feature of the patient anatomy in the first visual overlap having at least a minimum degree of alignment between the virtual representation and the physical patient anatomy, i.e. step S2. This identification of a well-aligned area and/or a well-aligned anatomical feature can be done manually by the user, e.g. by manually marking or highlighting the well-aligned area/feature in the displayed visual overlap. As mentioned, appropriate control means, like e.g. a joystick, for navigating through the mixed reality can be used for this, as the skilled reader will appreciated from this disclosure. Alternatively this can be done automatically by a processor, calculation unit or algorithm of a medical device of the present invention. In the latter computer-implemented alternative of identifying the well-aligned areas/features, the method can be seen as a computer-implemented medical method for registering the virtual representation with the coordinate system of the real, physical patient anatomy that is positioned on e.g. a patient bed in a preparation room, where the registration is carried out. The method further comprises displaying second overlap data in the head-mounted device, wherein the second overlap data describe from a second perspective onto the physical patient anatomy a second visual overlap between the virtual representation of the patient anatomy and the physical patient anatomy, step S3.

And the method takes into account, during the displaying of the second overlap data, the alignment of the identified first area and/or anatomical feature of the patient anatomy that was identified in the first visual overlap as having at least a minimum degree of alignment between the virtual representation and the physical patient anatomy, step S4. This beneficially ensures that the well alignment found from the first perspective, is not forgotten, but taken into account when the user continues the registration method in the next perspective. This leads to a fast converging registration method and the registration process can be finished much faster as compared to the prior art registration methods. Exemplary embodiments of this alignment can be taken into account while displaying the second overlap from the second perspective have been elucidated with various detailed embodiments that of course also apply to the FIG. 3 embodiment.

As is understood by the skilled reader from the present disclosure, the method defined by steps S1 to S4 does not rely on the known procedure of point pair matching for registering. Thus, the method presented does not predefine a plurality of points for the virtual representation and the physical anatomy of the patient in respective coordinate systems (i.e. coordinate system physical anatomy and coordinate system virtual representation), which are used for registering in point pair matching. This may be advantageous as point pair matching is very complex and time-consuming due to many necessary mathematical operations (e.g. deforming of the virtual representation in order to match single points, matching of the plurality of points, scaling of the virtual representation in order to match single points). Thus, as is understood by the skilled reader from the present disclosure, the method presented herein is different and in contrast to point pair matching for registering. The person skilled in registering understands, as is described herein in detail, that the present method is a marker-less method and/or a landmark-less method for registering a virtual representation of a patient anatomy with a coordinate system of a physical patient anatomy.

It should be noted that FIG. 3 shows an optional method step S8, which comprises two sub-steps. The step S8a of calculating the second overlap data, and the step S8b of minimizing, during the calculation of the second overlap data, the change of the degree of the alignment of the identified first area and/or of the first anatomical feature of the patient anatomy. With this optional embodiment, the method minimizes the impact of the desired movement initiated by the user onto the (already correctly achieved) alignment of the identified first area and/or identified first anatomical feature when calculating the second overlap data. Thus, based on the user input, the method may calculate an optimal solution for keeping the identified well-aligned features in the same or nearly the same alignment, as well as proceeding with the movement of the virtual representation as initiated by the user of the head-mounted device when he/she is in the second perspective.

Figure 4:
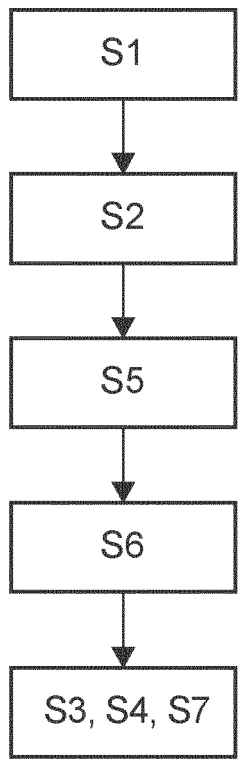
FIG. 4 shows another flow diagram of a method for registering a virtual representation of a patient anatomy with a coordinate system of a physical patient anatomy according to another exemplary embodiment of the present invention, and FIG. 5 schematically shows another method for registering a virtual representation of a patient anatomy with a coordinate system of a physical patient anatomy using an optimization according to an exemplary embodiment of the present invention.

The flow diagram of the method shown in FIG. 4 builds on the method described hereinbefore for FIG. 3 with respect to steps S1 to S4. It is thus referred to the description of S1 to S4 of FIG. 3. In addition to steps S1 to S4, a user input signal is received in step S5, which describes a movement of the virtual representation of the patient anatomy relative to the physical patient anatomy initiated by a user of the head-mounted device in the second perspective. Moreover, a change of the degree of the alignment of the identified first area and/or of the first anatomical feature of the patient anatomy caused by this movement of the virtual representation of the patient anatomy relative to the physical patient anatomy initiated by the user in the second perspective is calculated in step S6. This calculated change of the degree of alignment of the identified first area and/or of the first anatomical feature of the patient anatomy is then used in step S7 during the step displaying of the second overlap data, step S3. Thus, the use of the calculated change of the degree of alignment in step S7 can be seen a particular embodiment of step S4, in which the identified alignment of the first area/anatomical feature is taken into account during the displaying of the second overlap data.

Figure 5:
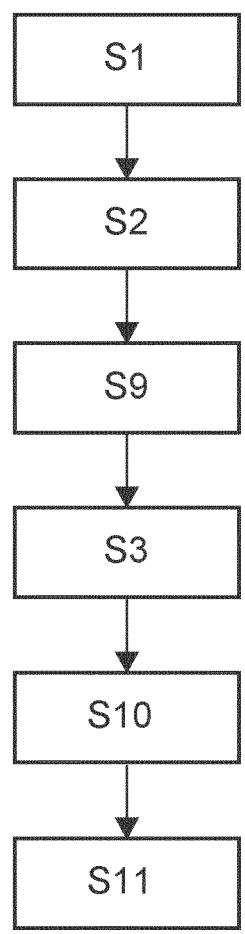

Furthermore, the flow diagram of the method shown in FIG. 5 builds on the method described hereinbefore for FIG. 3 with respect to steps S1 to S3. It is thus referred to the description of S1 to S4 of FIG. 3. Step S4, defining that the identified alignment of the first area/anatomical feature is taken into account during the displaying of the second overlap data, is embodied as a numerical optimization carried out in step S11, as will be explained in more detail hereinafter. In step S9, a user input signal describing a movement of the virtual representation of the patient anatomy relative to the physical patient anatomy initiated by a user of the head-mounted device in the second perspective is received, e.g. by a calculation unit 210 shown in FIG. 2. Similar to step S2, step S10 defines the identification of at least a second area in the second visual overlap and/or at least a second anatomical feature of the patient anatomy in the second visual overlap having at least a minimum degree of alignment between the virtual representation and the physical patient anatomy. As indicated before, a numerical optimization is carried out in step S11, which calculates an optimized movement of the virtual representation of the patient anatomy relative to the physical patient anatomy. In detail, this calculated and optimized movement minimizes a change of the degree of alignment of the first area and/or of the first feature from the first perspective, while maintaining or maximizing the degree of alignment of the second area and/or of the second feature from the second perspective between the virtual representation of the patient anatomy and the physical patient anatomy.

This embodiment of FIG. 5 describes that a user moves the model when he/she is in the second perspective and also that a second area/feature is identified, for which a good alignment, i.e. a high correlation or congruency, is identified. Based on the "suggested movement" caused by the user and the identified second area/feature, a numerical optimization is carried out thereby calculating "better movements". In other words, this embodiment optimizes the realignment of the virtual representation with the physical patient anatomy while ensuring that the impact of the realignment from the second perspective onto the previously identified well-alignment of the identified first area and/or first anatomical feature is minimized. An optimization algorithm may be used that takes into account both targets. First, the movement to be calculated shall maintain or maximize the degree of alignment of the second area and/or of the second feature from the second perspective. On the other hand, the movement to be calculated shall minimize a change of the degree of alignment of the first area and/or of the first feature from the first perspective.

In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope.

The invention claimed is:

1. A method for registering a virtual representation of a patient anatomy with a coordinate system of a physical patient anatomy, comprising:
    displaying first overlap data in a head-mounted device, wherein the first overlap data describe from a first perspective onto the physical patient anatomy a first visual overlap between the virtual representation of the patient anatomy and the physical patient anatomy,
    identifying at least a first area in the first visual overlap and/or at least a first anatomical feature of the patient anatomy in the first visual overlap having at least a minimum degree of alignment between the virtual representation and the physical patient anatomy,
    displaying second overlap data in the head-mounted device, wherein the second overlap data describe from a second perspective onto the physical patient anatomy a second visual overlap between the virtual representation of the patient anatomy and the physical patient anatomy, and
    taking into account, during the displaying of the second overlap data, the alignment of the identified first area and/or anatomical feature of the patient anatomy that was identified in the first visual overlap as having at least a minimum degree of alignment between the virtual representation and the physical patient anatomy.

2. Method according to claim 1, wherein the method does not use point pair matching for registering.

3. Method according to claim 1, wherein the first area and/or anatomical feature of the first overlap data and second overlap data is used for registering instead of point pair matching.

4. Method according to claim 1, wherein the method is carried out without a marker and/or a predefined landmark.

5. Method according to claim 1, wherein the first area and/or anatomical feature is identified by the user and/or by image processing.

6. Method according to claim 1, wherein the alignment of the identified first area and/or anatomical feature of the patient anatomy that was identified in the first visual overlap constrains an alignment of the identified first area and/or anatomical feature of the patient anatomy in the second visual overlap.

7. Method according to claim 1, the method further comprising:
receiving a user input signal describing a movement of the virtual representation of the patient anatomy relative to the physical patient anatomy initiated by a user of the head-mounted device in the second perspective,
calculating a change of the degree of the alignment of the identified first area and/or of the first anatomical feature of the patient anatomy caused by the movement of the virtual representation of the patient anatomy relative to the physical patient anatomy initiated by the user in the second perspective, and
using the calculated change of the degree of alignment of the identified first area and/or of the first anatomical feature of the patient anatomy for the displaying of the second overlap data.

8. Method according to claim 1, further comprising:
calculating the second overlap data, and
minimizing, during the calculation of the second overlap data, the change of the degree of the alignment of the identified first area and/or of the first anatomical feature of the patient anatomy.

9. Method according to claim 8,
wherein the change of the degree of the alignment of the identified first area and/or of the first anatomical feature of the patient anatomy is caused by a movement of the virtual representation of the patient anatomy relative to the physical patient anatomy initiated by the user of the head-mounted device in the second perspective.

10. Method according to claim 1, further comprising:
generating a control signal for the head-mounted device, wherein the control signal is configured for ensuring that the second visual overlap is only displayed to the user in the second perspective in case the alignment between the virtual representation and the physical patient anatomy of the identified first area and/or identified first anatomical feature does not change more than a predefined threshold value.

11. Method according to claim 1,
wherein the identified first area and/or the identified first anatomical feature of the patient anatomy are kept static during a realignment of the virtual representation of the patient anatomy and the physical patient anatomy by the user from the second perspective.

12. Method according to claim 1, further comprising:
blocking at least one degree of freedom out of three translational degrees of freedom and three rotational degrees of freedom of a movability of the virtual representation of the patient anatomy when the user is in the second perspective.

13. Method according to claim 12, further comprising:
generating a feedback signal for the user, which informs the user about the at least one blocked degree of freedom and/or about non-blocked degrees of freedom for initiating a movement of the virtual representation of the patient anatomy relative to the physical patient anatomy by the user of the head-mounted device in the second perspective.

14. Method according to claim 12, further comprising:
suggesting at least one perspective for the user based on blocked and/or non-blocked degrees of freedom.

15. Method according to claim 1, further comprising:
determining a constraint of a movability of the virtual representation of the patient anatomy relative to the physical patient anatomy based on the identified first area and/or of the identified first anatomical feature of the patient anatomy,
using the determined constraint for generating a control signal for the head-mounted device, and
restricting the movability of the virtual representation of the patient anatomy displayed to the user in the head-mounted device based on the determined constraint.

16. Method according to claim 15,
wherein the constraint is a fixed point and/or a fixed axis.

17. Method according to claim 1,
wherein identifying the first area and/or the first anatomical feature of the patient anatomy having the at least minimum degree of alignment between the virtual representation and the physical patient anatomy comprises:
detecting a visual overlap of at least one corresponding edge of the virtual representation and of the physical patient anatomy, detecting a visual overlap of at least one corresponding contour of the virtual representation and of the physical patient anatomy, and/or detecting a visual overlap of at least one corresponding visual gradient of the virtual representation and of the physical patient anatomy.

18. Method according to claim 1, further comprising:
automatically detecting that the user has moved from the first perspective into the second perspective.

19. Method according to claim 18,
wherein the automatic detection is carried out by tracking, preferably optically tracking, the head-mounted device relative to its surrounding.

20. Method according to claim 1, further comprising:
changing coordinates of the virtual representation of the patient anatomy within the coordinate system of the physical patient anatomy by moving the displayed virtual representation relative to the physical patient anatomy by a user of the head-mounted device.

21. Method according to claim 1, further comprising:
receiving a user input signal describing a movement of the virtual representation of the patient anatomy relative to the physical patient anatomy initiated by a user of the head-mounted device in the second perspective, and
generating a control signal for the head-mounted device for displaying the movement of the virtual representation of the patient anatomy relative to the physical patient anatomy in a display of the head-mounted device.

22. Method according to claim 21,
wherein the user input signal is generated by a user control means, e.g. a joystick, with which the user specifies a desired movement of the virtual representation of the patient anatomy relative to the physical patient anatomy.

23. Method according to claim 1, further comprising:
receiving a user input signal describing a movement of the virtual representation of the patient anatomy relative to the physical patient anatomy initiated by a user of the head-mounted device in the second perspective,
identifying at least a second area in the second visual overlap and/or at least a second anatomical feature of the patient anatomy in the second visual overlap having at least a minimum degree of alignment between the virtual representation and the physical patient anatomy, carrying out a numerical optimization, which calculates an optimized movement of the virtual representation of the patient anatomy relative to the physical patient anatomy, and wherein the optimized movement minimizes a change of the degree of alignment of the first area and/or of the first feature from the first perspective while maintaining or maximizing the degree of alignment of the second area and/or of the second feature from the second perspective between the virtual representation of the patient anatomy and the physical patient anatomy.

24. Method according to claim 1, further comprising:
displaying the second overlap data in the head-mounted device from the second perspective thereby transparently displaying to the user at least one area and/or at least one feature of the virtual representation of the patient anatomy, which prevents a direct view from the second perspective onto the identified first area and/or the identified first anatomical feature of the patient anatomy having the at least minimum degree of alignment.

25. Method according to claim 1,
displaying the second overlap data in the head-mounted device thereby also displaying a first perspective deviation indicator to the user,
wherein the first perspective deviation indicator indicates an alignment or misalignment between the virtual representation and the physical patient anatomy for the identified first area and/or the identified first anatomical feature of the patient anatomy having the at least minimum degree of alignment, and
wherein the alignment or misalignment is caused by a user input from the second perspective for moving the virtual representation relative to the physical patient anatomy.

26. Method according to claim 1, further comprising:
recording, from the first perspective, an image and/or video of the displayed first overlap data, and
displaying the recorded image and/or video in the head-mounted device while the user is in the second perspective and while the second overlap data are displayed to the user in the head-mounted device.

27. Method according to claim 1, further comprising:
providing sensor image data of at least one sensor within the head-mounted device, wherein the sensor image data depict from the first perspective the first visual overlap between the virtual representation of the patient anatomy and the physical patient anatomy,
wherein the identification of the first area and/or the first anatomical feature of the patient anatomy having the at least minimum degree of alignment between the virtual representation and the physical patient anatomy comprises:
comparing the provided sensor image data with the virtual representation of the patient anatomy thereby automatically identifying the first area and/or the first anatomical feature of the patient anatomy having the at least minimum degree of alignment between the virtual representation and the physical patient anatomy.

28. Method according to claim 1, further comprising:
determining six degrees of freedom of the movability of the virtual representation of the patient anatomy, wherein the six degrees of freedom are three translational degrees of freedom and three rotational degrees of freedom.

29. A non-transient computer readable medium which, when running on a computer or when loaded onto a computer, causes the computer to perform the method steps comprising:
displaying first overlap data in a head-mounted device, wherein the first overlap data describe from a first perspective onto a physical patient anatomy a first visual overlap between a virtual representation of the patient anatomy and the physical patient anatomy;
identifying at least a first area in the first visual overlap and/or at least a first anatomical feature of the patient anatomy in the first visual overlap having at least a minimum degree of alignment between the virtual representation and the physical patient anatomy;
displaying second overlap data in the head-mounted device, wherein the second overlap data describe from a second perspective onto the physical patient anatomy a second visual overlap between the virtual representation of the patient anatomy and the physical patient anatomy; and
taking into account, during the displaying of the second overlap data, the alignment of the identified first area and/or anatomical feature of the patient anatomy that was identified in the first visual overlap as having at least a minimum degree of alignment between the virtual representation and the physical patient anatomy.

30. A medical system for registering a virtual representation of a patient anatomy with a coordinate system of a physical patient anatomy, the medical system comprising
a calculation unit,
wherein the calculation unit is configured for
causing a displaying of first overlap data in a head-mounted device, wherein the first overlap data describe from a first perspective onto the physical patient anatomy a first visual overlap between the virtual representation of the patient anatomy and the physical patient anatomy,
identifying at least a first area in the first visual overlap and/or at least a first anatomical feature of the patient anatomy in the first visual overlap having at least a minimum degree of alignment between the virtual representation and the physical patient anatomy, and
displaying second overlap data in the head-mounted device, wherein the second overlap data describe from a second perspective onto the physical patient anatomy a second visual overlap between the virtual representation of the patient anatomy and the physical patient anatomy, and
taking into account, during the displaying of the second overlap data, the alignment of the identified first area and/or anatomical feature of the patient anatomy that was identified in the first visual overlap as having at least a minimum degree of alignment between the virtual representation and the physical patient anatomy.

31. Medical system according to claim 30, further comprising
a head-mounted device for displaying the first and second overlap data to the user.

* * * * *